US008398399B2

(12) United States Patent
Paschke

(10) Patent No.: US 8,398,399 B2
(45) Date of Patent: Mar. 19, 2013

(54) ULTRASONIC FLOSSING DEVICE

(76) Inventor: Richard H. Paschke, Timonium, MD (US)

( * ) Notice: Subject to any disclaimer, the term of this patent is extended or adjusted under 35 U.S.C. 154(b) by 426 days.

(21) Appl. No.: 12/670,802

(22) PCT Filed: Jul. 30, 2008

(86) PCT No.: PCT/US2008/071511
§ 371 (c)(1),
(2), (4) Date: Jan. 26, 2010

(87) PCT Pub. No.: WO2009/018292
PCT Pub. Date: Feb. 5, 2009

(65) Prior Publication Data
US 2010/0206324 A1    Aug. 19, 2010

Related U.S. Application Data

(60) Provisional application No. 60/962,512, filed on Jul. 30, 2007.

(51) Int. Cl.
*A61C 1/07* (2006.01)
*A61C 3/03* (2006.01)
*A61C 3/08* (2006.01)
(52) U.S. Cl. .................. 433/119; 433/124; 601/162
(58) Field of Classification Search ............. 433/80, 433/86, 89, 103, 118, 119, 131, 229; 601/2, 601/160, 162–165
See application file for complete search history.

(56) References Cited

U.S. PATENT DOCUMENTS

| | | | |
|---|---|---|---|
| 4,331,422 A * | 5/1982 | Heyman | 433/125 |
| 5,013,241 A | 5/1991 | von Gutfeld et al. | |
| 5,378,153 A * | 1/1995 | Giuliani et al. | 433/216 |
| 6,227,853 B1 * | 5/2001 | Hansen et al. | 433/119 |
| 2005/0142515 A1 * | 6/2005 | Levy et al. | 433/114 |
| 2005/0227201 A1 * | 10/2005 | Pond | 433/119 |
| 2007/0157404 A1 * | 7/2007 | Brewer et al. | 15/22.1 |
| 2007/0166663 A1 * | 7/2007 | Telles et al. | 433/119 |
| 2008/0209650 A1 * | 9/2008 | Brewer et al. | 15/22.1 |

OTHER PUBLICATIONS

International Search Report from PCT/US08/71511.

* cited by examiner

*Primary Examiner* — Nicholas Lucchesi
*Assistant Examiner* — Leah Stohr
(74) *Attorney, Agent, or Firm* — Carter, DeLuca, Farrell & Schmidt, LLP

(57) ABSTRACT

An ultrasonic flossing device includes a housing having a proximal portion and a distal portion. An engine is disposed within the housing and is configured to convert input energy into ultrasonic energy and an electronic driving circuit is coupled to both the engine and the power source. A power source is electrically coupled to the engine and is configured to deliver input energy to the engine. At least one acoustic transformer is coupled to the engine, the at least one acoustic transformer being configured to amplify the ultrasonic energy. A main fluid reservoir is configured to store a fluid therein, the main fluid reservoir being coupled to the at least one acoustic transformer such that, upon activation, the fluid transmits the ultrasonic energy to a treatment area.

28 Claims, 3 Drawing Sheets

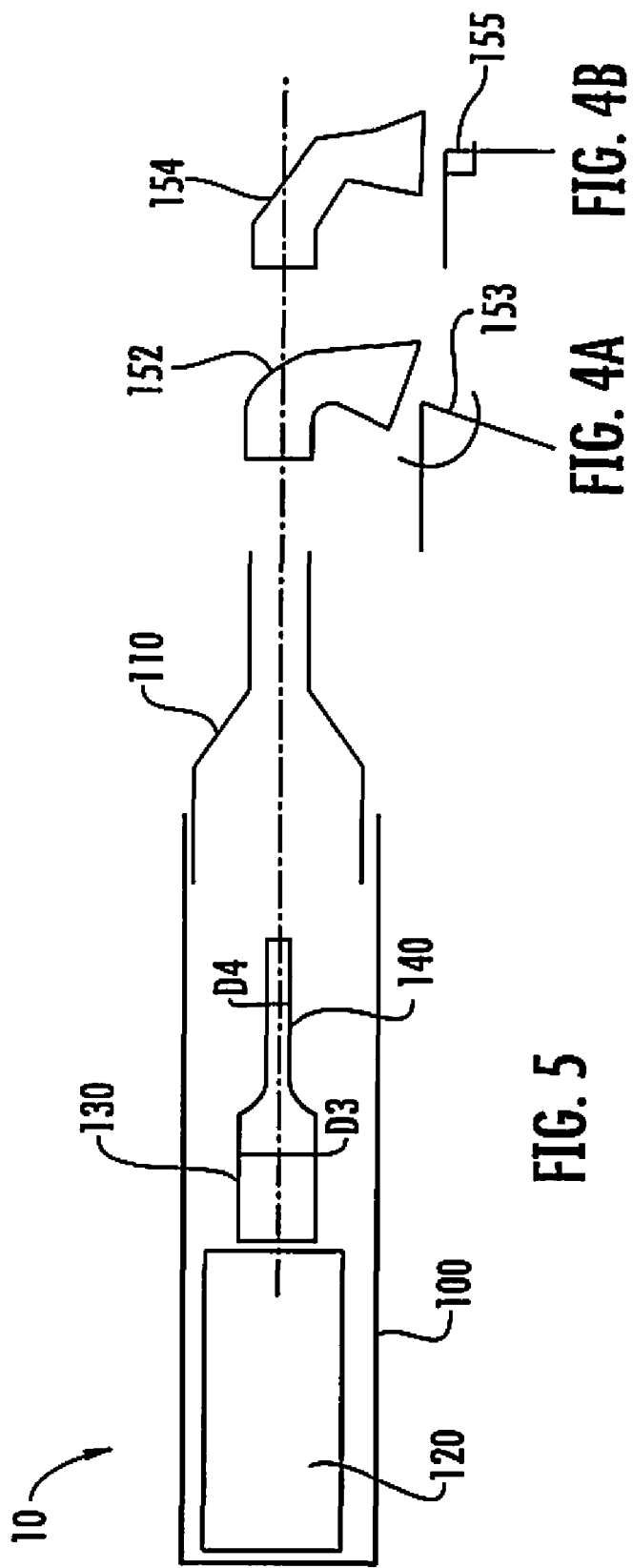

ULTRASONIC FLOSSING DEVICE

CROSS-REFERENCE TO RELATED APPLICATIONS

This application is a U.S. National Stage Application filed under 35 U.S.C. §371(a) of International Application No. PCT/US2008/071511, which claims the benefit of and priority to U.S. Provisional Application No. 60/962,512, filed on Jul. 30, 2007.

BACKGROUND

1. Technical Field

The present disclosure relates to an oral hygiene tool. More particularly, the present disclosure relates to an ultrasonic flossing device for disrupting debris and plaque from the surface of a person's teeth, between a person's teeth, or from the root surfaces.

2. Background of Related Art

The accumulation of plaque is a leading cause of periodontal disease. Flossing by hand to remove debris between teeth is effective in removing some of the debris and plaque between teeth. However, the shape of the teeth, especially the fluted areas on the root surfaces, reduces the effectiveness of flossing by hand with string floss tools. With the use of jet systems, the force of the water can cause discomfort when passing between the teeth and often creates an undesirable splashback when directed against a tooth surface.

SUMMARY

In accordance with the present disclosure, an ultrasonic flossing device is provided, the ultrasonic flossing device including a housing having a proximal portion and a distal portion. An engine is disposed within the housing and is configured to convert input energy into ultrasonic energy. The engine may be a magnetostriction transducer formed of Terfenol-D. The engine may alternatively be a piezoelectric transducer. An electronic driving circuit is coupled to both the engine and the power source. A power source is electrically coupled to the engine and is configured to deliver input energy to the engine. The power source may be a battery having a working voltage from about 3V to about 18V. At least one acoustic transformer is coupled to the engine and is configured to amplify the ultrasonic energy. The at least one acoustic transformer may have an operating frequency from about 15 kHz to 300 kHz. More specifically, the at least one acoustic transformer may have an operating frequency from about 18 kHz to about 32 kHz and a mechanical gain from about 1 to about 5. A main fluid reservoir is configured to store a fluid therein and is coupled to the at least one acoustic transformer such that, upon activation, the fluid transmits the ultrasonic energy to a treatment area. The main fluid reservoir may be releasably coupled to the housing.

The output voltage of the electronic driving circuit may be between the input voltage and 2 times the input voltage. The output voltage of the electronic driving circuit may also be operator controlled. A duty cycle of the output voltage of the electronic driving circuit may be between about 10% and about 100%.

In one embodiment, the main fluid reservoir includes a proximal base having a disc. The disc may have a non-uniform cross-section. A resonant frequency of the disc may be different from the operating frequency of the at least one acoustic transformer. The disc is sealingly attached to the main fluid reservoir via an elastomeric material. The main fluid reservoir further includes an open distal portion. The open distal portion of the main fluid reservoir may taper distally. A nozzle that is releasably coupled to the open distal portion of the main fluid reservoir may also be provided. The nozzle may be rotatable 360 degrees with respect to the housing and/or may be bent with respect to the housing.

The main fluid reservoir may be coupled to the at least one acoustic transformer via at least one magnet. The main fluid reservoir may be coupled to the at least one acoustic transformer via a first magnet disposed in mechanical cooperation with the at least one acoustic transformer and a second magnet disposed in mechanical cooperation with the disc of the main fluid reservoir. The first magnet and the second magnet may be configured such that the magnets repel each other or such that the magnets attract each other. An air gap may be defined between the first magnet and the second magnet.

In another embodiment, the main fluid reservoir is a nozzle. An elongated conduit is coupled to the at least one acoustic transformer at a proximal end and has a distal portion contained within the nozzle. The distal portion of the conduit may be bent at an angle between about 5 degrees to about 30 degrees, with respect to the housing. The nozzle may have a shaped distal portion and the shaped distal portion of the nozzle may be bent at an angle between about 5 degrees to about 30 degrees, with respect to the elongated conduit.

The ultrasonic flossing device may further include at least one ancillary fluid reservoir configured to store a fluid therein and adapted to fluidly connect to the main fluid reservoir.

BRIEF DESCRIPTION OF THE DRAWINGS

Embodiments of the presently disclosed ultrasonic flossing device are described herein with reference to the drawings, wherein:

FIG. 4A is a side view of a nozzle for the ultrasonic flossing device of FIG. 1;

FIG. 4B is a side view of a nozzle for the ultrasonic flossing device of FIG. 1;

FIG. 5 is an alternate embodiment of the ultrasonic flossing device of FIG. 2;

DETAILED DESCRIPTION OF THE EMBODIMENTS

Figure 2:
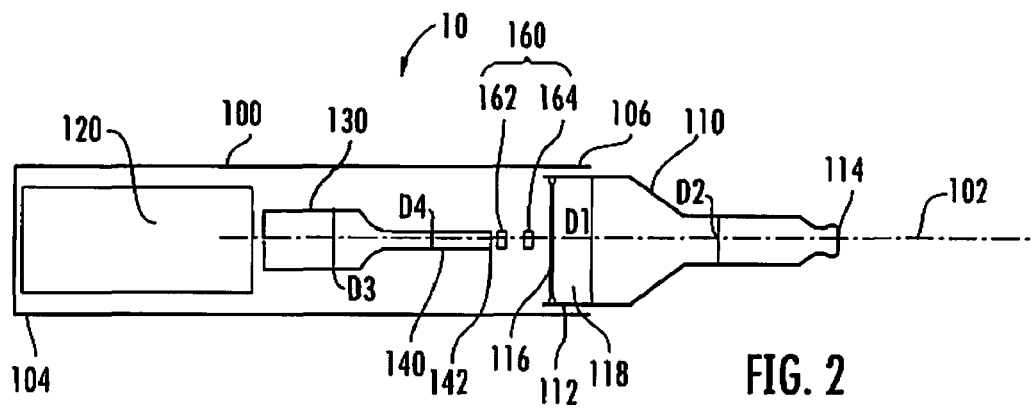
FIG. 2 is a side cross-sectional view of the ultrasonic flossing device of FIG. 1.

Embodiments of the presently disclosed ultrasonic flossing device will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

Figure 1:
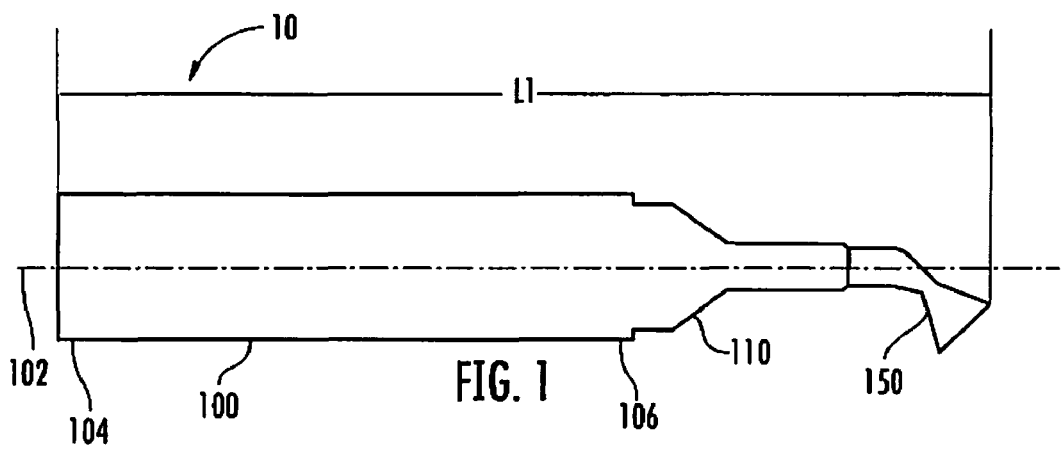
FIG. 1 is a side view of an ultrasonic flossing device in accordance with an embodiment of the present disclosure.

Referring now to the drawings, FIG. 1 illustrates an ultrasonic flossing device 10 including a housing 100 defining a longitudinal axis 102, a main fluid reservoir 110 and a nozzle 150.

As illustrated in FIG. 2, housing 100 includes a power source 120, an ultrasonic engine 130, and at least one acoustic transformer 140. An electronic driving circuit (part of element 120) is coupled to engine 130 and the power source 120. The power source 120 is coupled to the ultrasonic engine 130, which is coupled to the at least one acoustic transformer 140. The at least one acoustic transformer 140 is coupled to the main fluid reservoir 110. Generally, the power source 120 is configured to deliver input energy (e.g. electrical) to the ultrasonic engine 130, which converts the input energy into ultrasonic energy. The ultrasonic energy produced is in the form of acoustic vibrations. Accordingly, the ultrasonic engine 130 vibrates substantially axially with respect to the longitudinal axis 102 of the main fluid reservoir 110. The at least one acoustic transformer 140 amplifies the longitudinal displacement of the transducer 130 and communicates the amplified acoustic vibrations (i.e. ultrasonic energy) to the fluid contained within the main fluid reservoir 110. The activated (i.e. energized or ultrasonically agitated) fluid is then transmitted to a treatment area (not shown).

The power source 120 may be a replaceable or rechargeable battery with a working voltage from about 3 Volts to about 18 Volts. The power source 120 may further contain electronic circuitry (not shown) connectable to a user interface 300 (see FIG. 7) such that a user can control the operation of the ultrasonic flossing device 10. The user interface 300 will be described in more detail herein below.

The ultrasonic engine 130 may be a magnetostriction transducer, which may be made from Terfenol-D. Terfenol-D is an alloy of the formula TbDyFe and has higher energy density, a long life, and electric drive advantages. A Terfenol-D transducer is advantageous because it is a broadband device and therefore can operate with a simple electronic driver. Alternatively, the engine 130 may be a piezoelectric transducer. An important parameter of the ultrasonic engine 130 is the ultrasonic engine's electrical or magnetic energy to mechanical energy conversion efficiency. Both the Terfenol-D transducer and the piezoelectric transducer convert energy with greater than 90% efficiency. The ultrasonic engine system 130 vibrates and may have a displacement in the range of about 0.5 mils to about 1.5 mils. However, it is envisioned and within the scope of the present disclosure that the engine may be configured to have a vibrational displacement greater than or less than the above-mentioned range.

The motion of the ultrasonic engine 130 is coupled via at least one acoustic transformer 140, which acts as an amplifier for the ultrasonic engine 130. The at least one acoustic transformer 140 amplifies the vibrational motion of the transducer about 1 to about 5 times. A typical construction of the Terfenol-D transducer includes a tubular crystalline core which is under a compressive mechanical pre-load. The first acoustic transformer is an integral part of the construction and pre-load of the Terfenol-D transducer. The ratio of diameters of the acoustic transformer 140 and the Terfenol-D core helps to determine the mechanical gain of the combination. The mechanical gain of the combination may be about 1 to about 5. A drive coil (not shown) is wound around the Terfenol-D core. The coil is magnetically coupled to the ultrasonic engine 130. A combination of the mechanical pre-load and a medium to large field permanent magnet biases the Terfenol-D and places the ultrasonic engine 130 in a substantially linear area of operation.

In one embodiment, the at least one acoustic transformer 140 is configured such that the acoustic transformer 140 has an operating frequency of about 18 kHz to about 32 kHz. However, the at least one acoustic transformer 140 is not limited to an operating frequency in the above-mentioned range. The at least one acoustic transformer could have an operating frequency in the range of about 15 kHz to about 300 kHz. Further, the at least one acoustic transformer 140 may be configures as a system of acoustic transformers 140 with at least one quarter wavelength section. For example, the system of acoustic transformers 140 may range from about one quarter wavelength to a full wavelength.

The embodiment illustrated in FIG. 2 shows the power source 120 disposed within the housing 100 in the proximal portion 104 thereof. The Terfenol-D ultrasonic engine 130 is coupled to the power source 120. A system of acoustic transformers 140 is coupled to the ultrasonic engine 130. The main fluid reservoir 110 is disposed at a distal portion 106 of the housing 100 and is detachably engaged with the housing 100. The main fluid reservoir 110 may be detachably engaged with the housing by means including, but not limited to, a simple interference fit, a Bellville washer captured to the housing by a quarter turn thread or similar locking means, or a collar that captures both the housing 100 and main fluid reservoir 110. In some embodiments, the proximal base portion 112 of the main fluid reservoir 110 includes a disc 116 which is sealingly attached to the main fluid reservoir 110 via an elastomer material 118 such that the disc 116 acts as a diaphragm and is longitudinally and flexurally displaceable with respect to the main fluid reservoir 110. The main fluid reservoir 110 further includes an open distal portion 114. The shape of the open distal portion 114 may be a small frustum with its distal end having a feathered or tapered edge. Alternatively, a nozzle 150 may be releasably coupled to the open distal portion 114 of the main fluid reservoir 110. Different embodiments of the nozzle 150 are shown in FIGS. 4a and 4b. The embodiment of FIG. 4a shows a nozzle 152 with an open end, the open end being bent at an angle 153 of about 60 degrees with respect to a longitudinal axis 102 of the housing 100. The embodiment of FIG. 4b shows a nozzle 154 with an open end, the open end being bent at an angle 155 of about 90 degrees with respect to the longitudinal axis 102 of the housing 100. Simply by way of example, the open end of nozzle 154 is bent at an angle 155 of about 90 degrees, however it is envisioned that angle 155 may range from about 45 degrees to about 135 degrees. Generally, the nozzle 150 may also be rotatable up to 360 degrees with respect to the main fluid reservoir 110 such that the nozzle 150 can be adjusted to focus the ultrasonically activated fluid to different treatment areas for flossing and/or stain disruption. Different configurations for the open distal portion 114 of the main fluid reservoir 110 and the nozzle 150 are envisioned and within the scope of the present disclosure. These different configurations include any designs which help control the direction and velocity of the activated fluid as it is applied to a treatment area. These configurations will be readily apparent to those skilled in the art.

FIG. 2 further shows the acoustic transformer 140 coupled to the proximal portion 112 of the main fluid reservoir 110 via a system of magnets 160. A first magnet 162 is disposed in mechanical cooperation with a distal end 142 of the acoustic transformer 140. A second magnet 164 is disposed in mechanical cooperation with the disc 116 which forms the base of the main fluid reservoir 110. The coupling and polarity of the magnets 160 are arranged to provide effective coupling of the vibrational energy of the acoustic transformer 140. The first and second magnets 162, 164 may be configured such that they attract one another. Alternatively, the first and second magnets 162, 164 may be configured such that they repel one another. Further, the first and second magnets 162, 164 may be configured such that an air gap is defined therebetween or such that the first and second magnets 162, 164 are allowed to touch. In either embodiment, the motion of the ultrasonic engine 130 is amplified via the acoustic transformers 140 and coupled to the first magnet 162. The first magnet 162 moves in response to the acoustic vibrations, causing either attraction or repulsion with respect to the second magnet 164. Since the second magnet 164 is in mechanical cooperation with the disc 116, the disc 116, acting as a diaphragm, is longitudinally displaced as the second magnet 164 attracts or repels the first magnet 162. The disc 116 is able to act as a diaphragm because the disc 116 is attached to the main fluid reservoir 110 via an elastomer material 118. As the disc 116 is displaced according to the acoustic vibrations, coupling of the first and second magnets 160, and the mechanical characteristics of the diaphragm, the ultrasonic energy is transferred to the fluid within the main fluid reservoir 110. The ultrasonically activated fluid is then delivered to a treatment area via the open distal end 114 of the main fluid reservoir 110 or via the nozzle 150. The proximal portion 112 of the main fluid reservoir 110 may have a diameter D1 which is greater than the diameter of the second magnet 164. The proximal portion 112 of the main fluid reservoir 110 may also be configured such that diameter D1 is greater than the diameter D4 of the at least one acoustic transformer 140. The ratio of the diameters may provide a means to further increase the acoustic activity in the reservoir 110 or to control the type of acoustic activity in the reservoir 110. Additionally, the disc 116 may have a non-uniform cross-section such that the disc 116 had a greater thickness in the center and a smaller thickness near the edges (i.e. having a convex configuration). This configuration allows the amplitude of the acoustic vibrations to be substantially uniform across the surface of the disc 116. The disc may also be configured such that the disc has a resonant frequency which is different from the operating frequency of the at least one acoustic transformer. It is also envisioned that the at least one acoustic transformer 140 may be coupled to the main fluid reservoir 110 via a single magnet. The coupling would work in a similar manner as described above: the magnet would be responsive to the acoustic vibrations from the at least one acoustic transformer 140 and would transfer the ultrasonic energy to the fluid contained within the main fluid reservoir 110.

In one embodiment, the main fluid reservoir 110 is refillable. Once detached from housing 100, the main fluid reservoir 110 may be re-tilled with the appropriate fluid and re-attached to housing 100 for further use. Alternatively, the main fluid reservoir 110 may be disposable. After a single use, the main fluid reservoir 110 may be disposed of and a new main fluid reservoir 110 may be detachably engaged to the housing 100. Additionally, at least one ancillary fluid reservoir 170 may be configured to fluidly engage the main fluid reservoir 110 via ports 171, such that additional fluids may be delivered to a treatment area. The at least one ancillary fluid reservoir 170 may be configured to contain a variety of medicaments which aid in the oral hygiene/flossing process.

Figure 3:
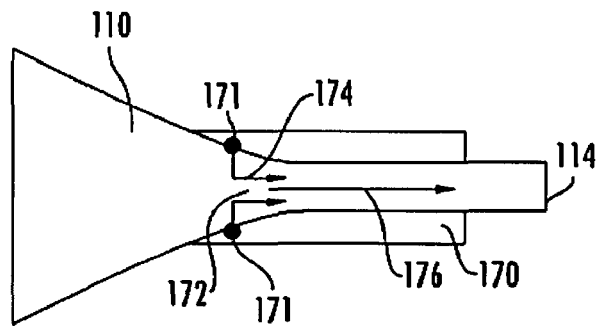
FIG. 3 is a side-cross sectional view of an embodiment of a main reservoir and an ancillary reservoir of the ultrasonic flossing device of the present disclosure.

Several configurations of the main fluid reservoir 110 are envisioned and within the scope of the present disclosure. In some embodiments, the main fluid reservoir 110 is a tapered tube configured to focus and amplify the ultrasonic intensity in the activated fluid toward a treatment area. For example, the diameter D1 may be greater than the diameter D2 such that the fluid is focused with greater ultrasonic intensity toward the open distal end 114 of the main fluid reservoir 110. The ratio of D1:D2 may be about 1 to about 7.5, depending on the desired intensity and/or focus of the fluid. The length and geometry of the reservoir is configured to optimize the action of the fluid and the delivery of the fluid to a treatment area. Such configurations will be readily apparent to those skilled in the art. As illustrated in FIG. 3, the main fluid reservoir 110 may also be configured with a nonlinear contour or shape, which allows the use of an ancillary reservoir 170 that may contain a variety of medicaments. The ancillary reservoir may be fluidly coupled to the main fluid reservoir via at least one port 171. The medicaments within the ancillary reservoir 170 are introduced into the main fluid reservoir 110 where the main fluid reservoir has an area of low pressure. The reduced pressure at the constriction point 172 allows the medicament to be introduced into the main fluid reservoir 110. The medicament enters the main fluid reservoir 110 through ports 171 in the direction of arrows 174 and is ultimately delivered out of the main fluid reservoir 110 (arrow 176) to a treatment area.

Figure 6:
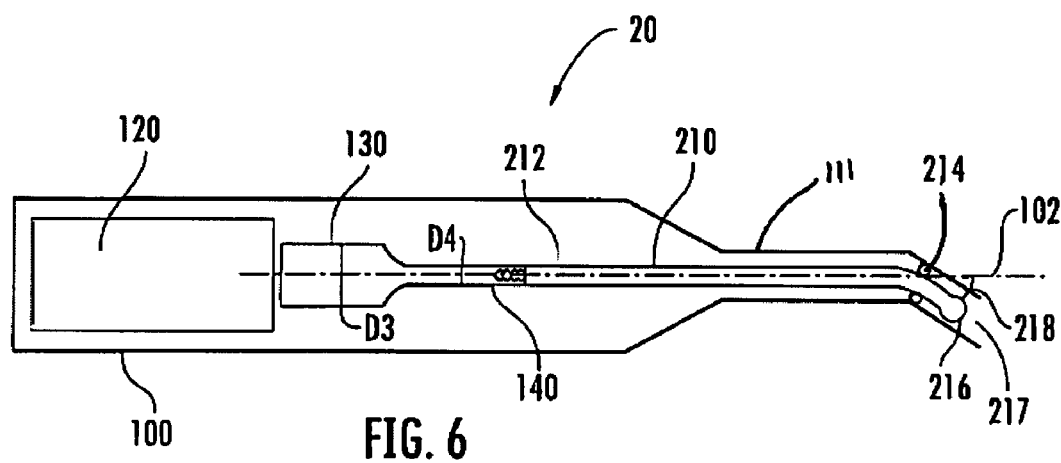
FIG. 6 is a further embodiment of the ultrasonic flossing device of FIG. 2.

Referring now to FIG. 6, another embodiment in accordance with the present disclosure is illustrated. Power source 120 coupled to ultrasonic engine 130 and at least one acoustic transformer 140 coupled to transducer 130 are disposed within housing 100 having distal portion 111. An elongated conduit 210 is at least partially disposed within distal portion 111 of housing 100 and coupled to the at least one acoustic transformer 140 at a proximal end 212 thereof. The elongated conduit 210 has a shaped distal portion 216. The shaped distal portion 216 may extend distally from distal portion 111 of housing 100. The shaped distal portion 216 of the elongated conduit 210 is configured to focus the ultrasonic energy to a treatment area. The shaped distal portion 216 of the elongated conduit 210 may also be bent at an angle 218 between about 5 degrees to about 30 degrees with respect to the longitudinal axis 102 of the elongated conduit 210. Further still, although illustrated as a rounded tip, the distal portion 216 may also be a flat tip. In this embodiment, the elongated conduit 210 couples the ultrasonic energy from acoustic transformer 140 to nozzle 152 or 154 (see FIGS. 4A-B), which act as the fluid reservoir. Upon activation, the fluid is ultrasonically agitated and delivered to a treatment area. An elastomeric seal 214 (e.g. an O-ring) may be disposed in mechanical cooperation with the distal portion 216 of the elongated conduit 210 and the distal portion 111 of housing 100, such that the ingress of fluid into housing 100 is substantially prevented. Further, distal portion 111 of housing 100 may extend beyond the distal end 216 of conduit 210, forming a gap 217 therebetween that prevents the shaped end of the conduit from contacting the treatment area.

Figure 7:
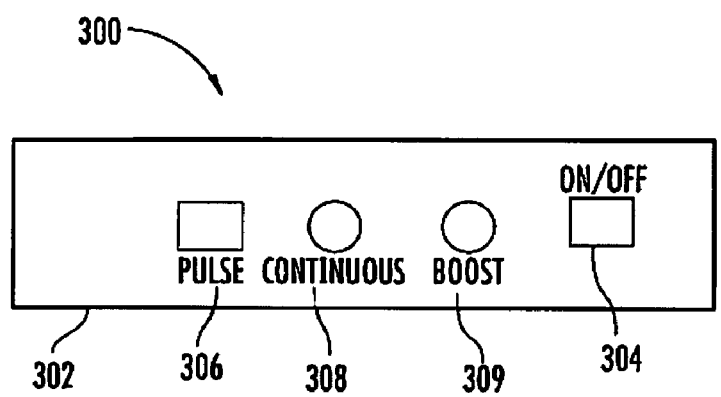
FIG. 7 is a front plan view of a controller for the ultrasonic flossing device of the present disclosure.

Referring now to FIG. 7, a user interface 300 is shown. User interface 300 includes controller 302, an on/off switch 304, as well as operational mode buttons including pulse 306, continuous 308, and boost 309. The ultrasonic engine 130 (see FIGS. 2, 5 & 6) is adaptable to be driven by a continuous signal of varying wave shapes or by pulsed means. The user may select which operating mode is desired. A number of other user-controlled preferred functions are also envisioned and within the scope of the present disclosure. These preferred functions include, but are not limited to, timed operation, and boost function.

In one embodiment, the electronic driving circuit (not shown), which is coupled to the ultrasonic engine 130 and the power source 120, is configured such that the output voltage created by the electronic driving circuit is between the input voltage (from the power source 120) and two times the input voltage. The duty cycle of the output voltage may be between about 10% and about 100%. The electronic driving circuit may also be operator controlled, via controller 302. In such an embodiment, controller 302 would further include a boost button 309, configured to cause the electronic driving circuit to increase the output voltage. The boost function may be time dependent and may operate in about 1 to about 5 second intervals.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An ultrasonic device, comprising:
   a housing having a proximal portion and a distal portion;
   an engine disposed within the housing and configured to receive input energy, convert the input energy into ultrasonic energy, and output the ultrasonic energy;
   a power source coupled to the engine and configured to deliver the input energy to the engine;
   at least one acoustic transformer disposed within the housing and coupled to the engine, the at least one acoustic transformer configured to receive the ultrasonic energy, amplify the ultrasonic energy, and output the amplified ultrasonic energy;
   a main fluid reservoir coupled to the housing and the at least one acoustic transformer, the main fluid reservoir configured to store a liquid therein and receive the amplified ultrasonic energy and defining a nozzle having a shaped distal portion;
   and an elongated conduit disposed within the housing and coupled between the at least one acoustic transformer and the main fluid reservoir, wherein the shaped distal portion of the nozzle of the main fluid reservoir is bent at an angle between about 5 degrees and about 30 degrees with respect to the elongated conduit,
   wherein, receipt of the amplified ultrasonic energy by the main fluid reservoir energizes the fluid stored within the main fluid reservoir and transfers the energized fluid from the main fluid reservoir to a treatment area.

2. The ultrasonic device of claim 1, wherein the engine is a magnetostriction transducer.

3. The ultrasonic device of claim 2, wherein the magnetostriction transducer is made from Terfenol-D.

4. The ultrasonic device of claim 1, wherein the engine is a piezoelectric transducer.

5. The ultrasonic device of claim 1, wherein the power source includes a battery disposed within the housing.

6. The ultrasonic device of claim 5, wherein the battery has a working voltage from about 3V to about 18V.

7. The ultrasonic device of claim 1, wherein the at least one acoustic transformer has an operating frequency from about 15 kHz to about 100 kHz.

8. The ultrasonic device of claim 1, wherein the at least one acoustic transformer has an operating frequency from about 18 kHz to about 32 kHz.

9. The ultrasonic device of claim 1, wherein the at least one acoustic transformer has a mechanical gain from about 1 to about 5.

10. The ultrasonic device of claim 1, further comprising an electronic driving circuit coupled between the engine and the power source, the electronic driving circuit configured to receive an input voltage from the power source and output an output voltage to the engine.

11. The ultrasonic device of claim 10, wherein the output voltage of the electronic driving circuit is between the input voltage and 2 times the input voltage.

12. The ultrasonic device of claim 10, wherein the output voltage of the electronic driving circuit is operator controlled.

13. The ultrasonic device of claim 10, wherein a duty cycle of the output voltage of the electronic driving circuit is between about 10% and about 100%.

14. The ultrasonic device of claim 1, wherein at least one of the acoustic transformers has an operating range of about ¼ wavelength to about 1 wavelength.

15. The ultrasonic device of claim 1, wherein at least one of the acoustic transformers is a ¼ wavelength acoustic transformer.

16. An ultrasonic device, comprising:
   a housing having a proximal portion and a distal portion;
   an engine disposed within the housing and configured to receive input energy, convert the input energy into ultrasonic energy, and output the ultrasonic energy;
   a power source coupled to the engine and configured to deliver the input energy to the engine;
   at least one acoustic transformer disposed within the housing and coupled to the engine, the at least one acoustic transformer configured to receive the ultrasonic energy, amplify the ultrasonic energy, and output the amplified ultrasonic energy; and
   a main fluid reservoir coupled to the housing and the at least one acoustic transformer and configured to store a fluid therein and receive the amplified ultrasonic energy, the main fluid reservoir including a proximal base and an open distal portion, the proximal base having a disc sealingly attached thereto via an elastomer material, the open distal portion including a nozzle releasably coupled thereto,
   wherein, receipt of the amplified ultrasonic energy by the main fluid reservoir energizes the fluid stored within the main fluid reservoir and transfers the energized fluid from the main fluid reservoir to a treatment area.

17. The ultrasonic device of claim 16, wherein the main fluid reservoir is releasably coupled to the housing.

18. The ultrasonic device of claim 16, wherein the open distal portion of the main fluid reservoir tapers distally.

19. The ultrasonic device of claim 16, wherein the nozzle is rotatable 360 degrees with respect to the housing.

20. The ultrasonic device of claim 16, wherein the nozzle is bent with respect to the housing.

21. The ultrasonic device of claim 16, wherein the main fluid reservoir is coupled to the at least one acoustic transformer via at least one magnet.

22. The ultrasonic device of claim 21, wherein the main fluid reservoir is coupled to the at least one acoustic transformer via a first magnet disposed in mechanical cooperation with the at least one acoustic transformer and a second magnet disposed in mechanical cooperation with the disc of the main fluid reservoir.

23. The ultrasonic device of claim 22, wherein the first magnet and the second magnet are configured such that the magnets repel each other.

24. The ultrasonic device of claim 22, wherein the first magnet and the second magnet are configured such that the magnets attract each other.

25. The ultrasonic device of claim 22, wherein an air gap is defined between the first magnet and the second magnet.

26. The ultrasonic device of claim 16, further comprising at least one ancillary fluid reservoir configured to store a fluid therein and adapted to fluidly connect to the main fluid reservoir.

27. The ultrasonic device of claim 16, wherein the disc has a non-uniform cross-section.

28. The ultrasonic device of claim 16, wherein a resonant frequency of the disc is different than the operating frequency of the at least one acoustic transformer.

* * * * *